United States Patent [19]

Bishop et al.

[11] Patent Number: 4,537,505
[45] Date of Patent: Aug. 27, 1985

[54] METHOD FOR DETECTING PIN HOLES AND THE LIKE IN SHEET MATERIAL FOR PACKAGING AND SIMILAR APPLICATIONS

[75] Inventors: Robert Bishop, Brookline; Krikor Bezjian, Cambridge, both of Mass.

[73] Assignee: Beltronics Inc., Brookline, Mass.

[21] Appl. No.: 407,097

[22] Filed: Aug. 11, 1982

[51] Int. Cl.$^3$ .............................................. G01N 21/89
[52] U.S. Cl. ....................................... 356/237; 250/572
[58] Field of Search ........................ 356/236, 237, 239; 250/572, 228

[56] References Cited

U.S. PATENT DOCUMENTS

| | | | |
|---|---|---|---|
| 2,444,442 | 7/1948 | Herbold | 250/237 R X |
| 3,422,272 | 1/1969 | Brosious et al. | 356/237 X |
| 3,541,340 | 11/1970 | Binks | 356/237 X |
| 3,710,129 | 1/1973 | Gibson | 356/237 X |
| 3,991,882 | 11/1976 | Fahnestock et al. | 356/237 X |
| 4,120,582 | 10/1978 | DeVries et al. | 356/236 X |

*Primary Examiner*—Vincent P. McGraw
*Attorney, Agent, or Firm*—Rines and Rines, Shapiro and Shapiro

[57] ABSTRACT

This disclosure is concerned with the optical detection of pin holes or similar aberrations in sheet material, such as metal or metalized packaging materials that are to enclose and seal contents therewithin, with the aid of a reflective-wall cavity structure over which the sheet material is placed and light-sealed and the walls of which are shaped to enable external light leaking through the pin hole or the like to become multiply reflected from the cavity walls and the underside of the sheet to impinge upon photodetecting means at an appropriate portion of the walls, thus to enable detection of such leak, and, if desired, location of the pin hole or the like.

5 Claims, 1 Drawing Figure

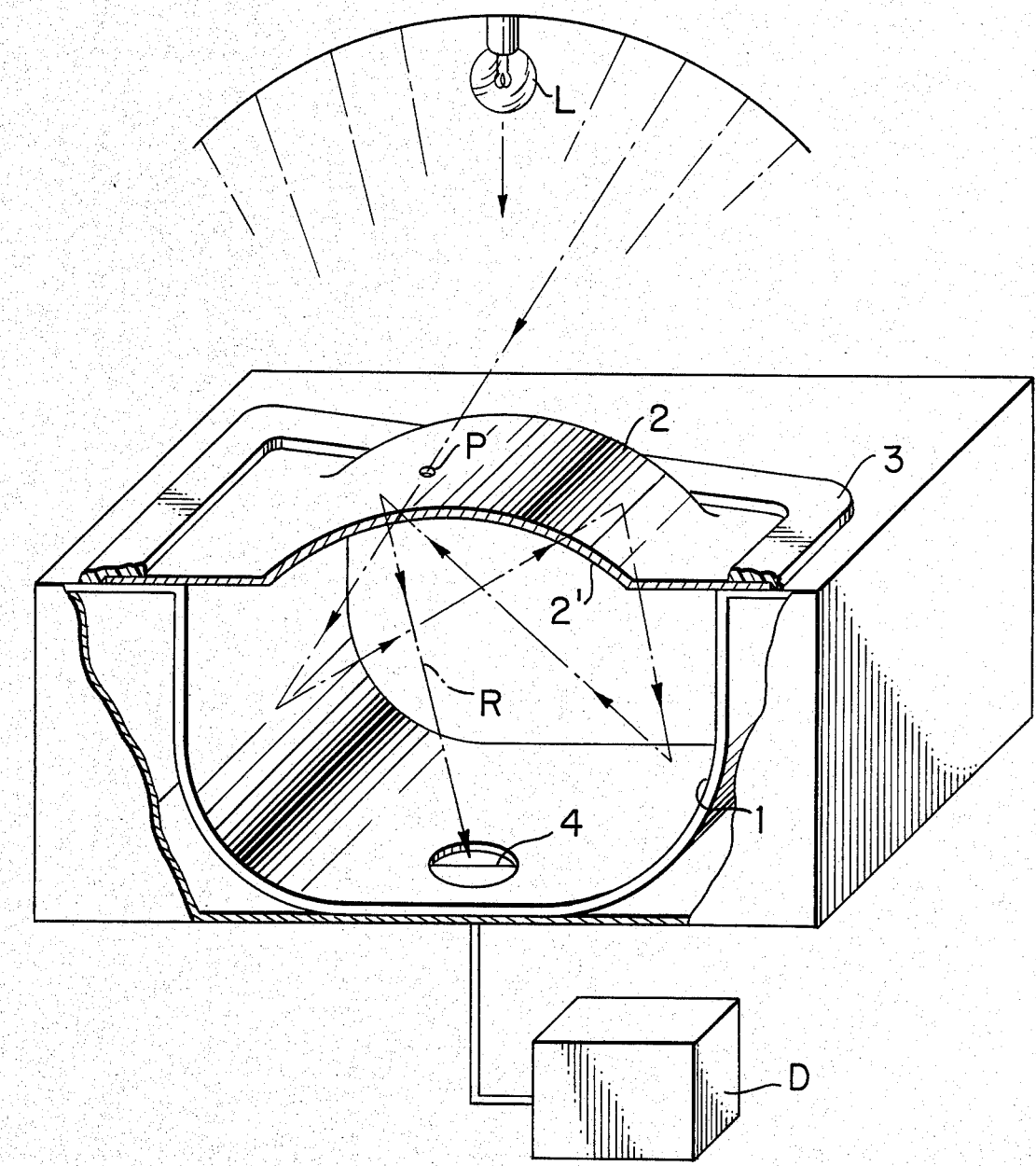

METHOD FOR DETECTING PIN HOLES AND THE LIKE IN SHEET MATERIAL FOR PACKAGING AND SIMILAR APPLICATIONS

The present invention relates to methods of and apparatus for detecting pin-holes or similar aberrations or the like in sheet material, such as metal or metalized packaging materials that are to seal and enclose contents therewithin, being more particularly directed to the automatic optical detection of the presence of such pin holes and, if desired, precise location thereof.

There are numerous industrial and related requirements for sheet material that is gas, vapor or liquid impervious, as for such purposes as providing a sealed enclosure or a package that may contain articles, solutions, atmospheres, sterilized or treated materials, medical or food products or other substances and materials which must be totally sealed from the environment in which the package or enclosure is placed. Similar problems also exist in closing off other types of enclosures than packages. While careful manufacturing techniques may be employed in the reliable production or shaping of such sheet materials, it is not possible always to insure the absence of small perforations, cuts or breaks or similar aberrations, hereinafter generically referred to as pin holes or pin holes and the like; and many of such are not readily detectable either by the human eye in normal observation or by conventional back-lighting or similar optical scanning or monitoring systems. In the preparation of aluminum foil and other metal or metalized packaging sheets for packaging sterilized medical devices and materials or food or liquid products and the like, particularly where such materials are formed or shaped into various geometrical package configurations, the problem of insuring against such pin holes before the package material receives the product and is sealed thereabout still plagues the art; one of the current commercial techniques still involving an archaic time- and personnel-consuming process of having several operators separately inspect the sheet material against lights in a dark room, often with magnifying glasses.

An object of the present invention is to provide a new and improved pin-hole detecting method and apparatus that obviate these problems and provide for the automatic and facile optical detection of such pin holes with high reliability and with a simple procedure for locating the precise region of the pin hole if mere detection of the presence of a pin hole alone is not sufficient for the particular application.

A further object is to provide a novel optical detecting method and apparatus of more general utility, as well.

Other and further objects will be explained hereinafter and are more particularly delineated in the appended claims.

In summary, however, from one of its important aspects, the invention embraces a method of pin-hole detection in a sheet to be used as part of a sealed enclosure, that comprises, placing the sheet over an open-mouth light-reflecting walled cavity; light-sealing the periphery of the sheet over the cavity mouth; brightly illuminating the outer surface of the sheet to cause light to leak through any pin hole therein into the cavity; shaping the light-reflecting cavity walls to insure multiple and randomly distributed light reflections including from the inner surface of the sheet within the cavity as light enters the pin hole; and detecting a signal from such multiply reflected light at a predetermined region within the cavity which statistically will receive at least part of such multiply reflected light to register the presence of the pin hole. Preferred embodiments and details and best mode example are hereinafter presented.

The invention will now be described with reference to the accompanying drawing, the single FIGURE of which is a combined isometric view and circuit diagram illustrating the invention in preferred form.

Referring to the drawing, a box-type cavity 1 is shown provided with light-reflective walls, preferably with the corners curved in somewhat bowl shape for providing multiple and random reflecting surfaces. A sheet that is to be inspected for pin holes and the like, as of aluminum or other metallized packaging material, or other material intended to provide sealed packages or surfaces and the like, is shown at 2, placed over the mouth of the cavity 1 and light-sealed as at 3 to the periphery of the mouth as by masking tape or gasket. The sheet 2, for best operation of the invention, has a light-reflective inner surface 2' so that extended light from an intense source L, brightly illuminating the outer surface of the sheet 2 can leak through any pin hole, such as shown at P, into the cavity 1 and will be subjected to statistically sufficient multiple and random reflections between the cavity walls and between the same and the inner sheet surface 2' to insure over a short period of time the receipt of at least part of such multiply reflected light (R) at a photodetector 4, shown disposed at a preferred predetermined central region of the bottom reflective wall of the cavity 1. The receipt of the light leaked through the pin hole P will be registered and indicated in the amplifier and detector D to indicate the presence of a pin hole.

With a cavity 1 of dimensions $2'' \times 6'' \times 2''$, the walls of which were shaped from metallized mylar sheeting with curved corners of about 4" radius, and light source L of 100 watts, pin holes in aluminum sheets 2 of about 200 microns or less in thickness have been consistently detected with a photodetector 4 of the UDT-PIN10 type, and an amplifier D, producing signals of the order of 200 millivolts to 1 volt or greater, clearly identifying the presence of the pin hole.

By covering successive small areas of the outer surface of the sheet 2, the appearance and disappearance of the signal at D will readily identify the location of the pin hole P, if such location is desired.

The walls of the cavity may be otherwise shaped to attain the multiple-reflection randomized effect, and supplemental photo detectors may also be used at different predetermined regions of the cavity, such and further modifications as will readily occur to those skilled in this art being considered to fall within the spirit and scope of the invention as defined in the appended claims.

What is claimed is:

1. A method of pin-hole detection in a sheet to be used as part of a sealed enclosure, that comprises, placing the sheet over an open-mouth light-reflecting or light-scattering walled cavity; light-sealing the periphery of the sheet over the cavity mouth; brightly illuminating the outer surface of the sheet to cause light to leak through any pin hole therein into the cavity; shaping the light-reflecting cavity walls to insure multiple and randomly distributed light reflections including from the inner surface of the sheet within the cavity as light enters the pinhole; and detecting a signal from such multiply reflected light at a predetermined region within the cavity which statistically will receive at least part of such multiply reflected light to register the presence of the pin hole.

2. A method as claimed in claim 1 and in which at least the said inner surface of the sheet is of reflective metal and said cavity walls are curved at least in part to insure the random multiple reflection distribution.

3. A method as claimed in claim 1 and in which the multiple reflected light detecting is effected at an intermediate region of a reflective wall of the cavity.

4. A method as claimed in claim 3 and in which said reflective wall is the wall opposite said sheet.

5. A method as claimed in claim 1 and in which, following the detecting of the pin-hole light leak the location of the same on the sheet is effected by successively covering and uncovering small successive incremental portions of the said outer surface of the sheet to detect the disappearance and appearance, respectively, of the said signal.

* * * * *